(12) United States Patent
Tidmarsh

(10) Patent No.: US 8,318,683 B2
(45) Date of Patent: Nov. 27, 2012

(54) ANTI-CANCER THERAPIES

(75) Inventor: George Tidmarsh, Portola Valley, CA (US)

(73) Assignee: Threshold Pharmaceuticals, Inc., South San Francisco, CA (US)

( * ) Notice: Subject to any disclaimer, the term of this patent is extended or adjusted under 35 U.S.C. 154(b) by 1026 days.

(21) Appl. No.: 10/588,409

(22) PCT Filed: Feb. 4, 2005

(86) PCT No.: PCT/US2005/003370
§ 371 (c)(1),
(2), (4) Date: May 6, 2009

(87) PCT Pub. No.: WO2005/076888
PCT Pub. Date: Aug. 25, 2005

(65) Prior Publication Data
US 2009/0247480 A1    Oct. 1, 2009

Related U.S. Application Data

(60) Provisional application No. 60/542,494, filed on Feb. 6, 2004.

(51) Int. Cl.
*A61K 31/7028* (2006.01)
*A61K 31/7008* (2006.01)
*A61P 35/04* (2006.01)

(52) U.S. Cl. ............................ 514/25; 514/49
(58) Field of Classification Search ................. None
See application file for complete search history.

(56) References Cited

U.S. PATENT DOCUMENTS

| 4,808,614 | A | 2/1989 | Hertel |
| 5,464,826 | A | 11/1995 | Grindey et al. |
| 5,622,936 | A | 4/1997 | Wiessler et al. |
| 6,489,302 | B1 | 12/2002 | Wiessler et al. |
| 2004/0136950 | A1 | 7/2004 | Ni et al. |
| 2004/0167079 | A1 | 8/2004 | Tidmarsh |
| 2005/0054708 | A1 | 3/2005 | Michols et al. |

FOREIGN PATENT DOCUMENTS

| EP | 1711188 A2 | 8/2005 |
| WO | WO 2006/071955 A2 | 7/2006 |
| WO | WO 2006/122227 A1 | 11/2006 |
| WO | WO 2007/035961 A1 | 3/2007 |

OTHER PUBLICATIONS

Briasoulis, E. et al., European Journal of Cancer, "Glufosfamide administered using a 1-hour infusion given as first-line treatment for advanced pancreatic cancer. A phase II trial of the Eortc-new drug development group", 2003, vol. 39, pp. 2334-2340.*
Giaccone, G. et al., European Journal of Cancer, "Glufosfamide administered by 1-hour infusion as a second-line treatment for advanced non-small cell lung cancer: a phase II trial of the EORTC-New Drug Development Group", published online Jan. 2004, vol. 40, pp. 667-672.*

Author is Anonymous, Drug R&D, "Glufosfamide", Feb. 1, 2005, vol. 6, No. 1, pp. 49-52.*
U.S. Appl. No. 60/910,403, Handisides et al.
Araneo et al., "Biweekly Low-Dose Sequential Gemcitabine, 5-Fluorouracil, Leucovorin, and Cisplatin (GFP): A Highly Active Novel Therapy for Metastatic Adenocarcinoma of the Exocrine Pancreas," *Cancer Invest.*, 21(4):489-496 (2003).
Briasoulis et al., "Phase I Trial of 6-Hour Infusion of Glufosfamide, a New Alkylating Agent With Potentially Enhanced Selectivity for Tumors That Overexpress Transmembrane Glucose Transporters: A Study of the European Organization for Research and Treatment of Cancer Early Clinical Studies Group," *J. Clin Oncol*, 18(20):3535-3544 (2000).
Burris et al., "Assessing Clinical Benefit in the Treatment of Pancreas Cancer: Gemcitabine Compared to 5-Fluorouracil," *Eur. J. Cancer*, 33(Suppl 1):S18-S22 (1997).
Kozuch et al., "Irinotecan Combined with Gemcitabine, 5-Fluorouracil, Leucovorin, and Cisplatin (G-FLIP) is an Effective and Noncrossresistant Treatment for Chemotherapy Refractory Metastatic Pancreatic Cancer," *The Oncologist*, 6:488-495 (2001).
Niculescu-Duvaz, I., "Glufosfamide (Baxter Oncology)," *Curr. Opin. Investig. Drugs*, 3(10):1527-1532 (2002).
Noble et al., "Gemcitabine. A review of its Pharmacology and Clinical Potential in Non-Small Cell Lung Cancer and Pancreatic Cancer," *Drugs*, 54(3): 447-472 (1997).
Rothenberg et al., "A phase II trial of gemcitabine in patients with 5-FU-refractory pancreas cancer," *Ann. Oncol.*, 7:347-353 (1996).
Stephens, C. D., "Gemcitabine: A New Approach to Treating Pancreatic Cancer," *Oncol. Nurs. Forum* 25(1):87-93 (1998).
Ziske et al., "Prognostic value of CA 19-9 levels in patients with inoperable adenocarcinoma of the pancreas treated with gemcitabine," *Br. J. Cancer*, 89:1413-1417 (2003).
"Threshold Pharmaceuticals Announces That a Phase 3 Clinical Trial of Glufosfamide for Treatment of Pancreatic Cancer Did Not Meet Its Primary Endpoint", News Release, Threshold Pharmaceuticals Inc., Feb. 27, 2007.
Cancer Drug Information, National Cancer Institute : 7 pages, retrieved on Oct. 6, 2011 from <URL: http://www.cancer.gov/cancertopics/druginfo/alphalist>. Chiorean et al., "A Phase 2 Trial of Glufosfamide in Combination With Geemcitabine in Chemotherapy-Naïve Pancreatic Adenocarcinoma," *American Journal of Clinical Oncology*, 33(2):111-116 (Apr. 2010).
Ciuleanu et al., "A Randomized Phase III Trial of Glufosfamide Compared With Best Supportive Care in Metastatic Pancreatic Adenocarcinoma Previously Treated With Gemcitabine," European Journal of Cancer 45:1589-1596 (2009).
Hertzberg et al., "Outpatient-Based Ifosfamide, Carboplatin and Etoposide (ICE) Chemotherapy in Transplant-Eligible Patients With Non-Hodgkin's Lymphoma and Hodgkin's Disease," *Annals of Oncology*, 14(Supplement 1):i11-i16 (2003).

(Continued)

*Primary Examiner* — Shaojia Anna Jiang
*Assistant Examiner* — Bahar Craigo
(74) *Attorney, Agent, or Firm* — Kilpatrick Townsend & Stockton LLP

(57) ABSTRACT

Methods for the treatment of cancer are described. In particular, methods for treatment of cancer comprising administration of glufosfamide alone or in combination with another anticancer agent are disclosed.

17 Claims, No Drawings

OTHER PUBLICATIONS

Okada et al., "Phase I Trial of Gemcitabine in Patients with Advanced Pancreatic Cancer," Jpn. J. Clin Oncol., 31(1)7-12 (2001).

Seker et al., "Mechanistic Aspects of the Cytotoxic Activity of Glufodfamide, a New Tumor Therapeutic Agent," British Journal of Cancer, 82(3):629-634 (2000).

Smith et al., A Phase II/III Study Comparing Intravenous ZD9331 With Gemcitabine in Patients With Pancreatic Cancer, *European Journal of Cancer*, 39(10):1377-1383 (Jul. 1, 2003).

Tarceva Erlotinib Tablets—Highlights of Prescription Information, 6 Pages, Revised Apr. 2010.

European Supplementary Report dated Aug. 26, 2009 from European Patent Application No. EP 05712714.

Notice to File a Response (Preliminary Rejection) from Korean Patent Application No. 10-2006-7017702 dated Aug. 16, 2011.

* cited by examiner

ANTI-CANCER THERAPIES

CROSS-REFERENCE TO RELATED APPLICATION

This application claims benefit of U.S. provisional patent application No. 60/542,494, filed 6 Feb. 2004, which is incorporated herein by reference.

TECHNICAL FIELD

The present invention relates generally to methods for the treatment of cancer. In particular, the invention relates to methods of treating cancer comprising administration of glufosfamide alone or in combination with another anticancer agent.

BACKGROUND OF THE INVENTION

"Cancer" refers generally to one of a group of more than 100 diseases caused by the uncontrolled, abnormal growth of cells that can spread to adjoining tissues or other parts of the body. Cancer cells can form a solid tumor, in which the cancer cells are massed together, or exist as dispersed cells, as in leukemia. Normal cells divide (reproduce) until maturation is attained and then only as necessary for replacement of damaged or dead cells. Cancer cells are often referred to as "malignant", because they divide endlessly, eventually crowding out nearby cells and spreading to other parts of the body. The tendency of cancer cells to spread from one organ to another or from one part of the body to another distinguishes them from benign tumor cells, which overgrow but do not spread to other organs or parts of the body. Malignant cancer cells eventually metastasize and spread to other parts of the body via the bloodstream or lymphatic system, where they can multiply and form new tumors. This sort of tumor progression makes cancer a deadly disease. Although there have been great improvements in the diagnosis and treatment of cancer, many people die from cancer each year, and their deaths are typically due to metastases and cancers that are resistant to conventional therapies. Current methods for treatment of advanced and/or metastatic malignancies previously treated with chemotherapy (i.e. chemotherapy-refractory cancers) are inadequate. Curative therapy is not possible in patients with advanced malignancies that have relapsed after chemotherapy.

There is a need in the art for improved methods for the treatment of advanced and/or metastatic malignancies previously treated with chemotherapy. The present invention addresses these needs and provides for methods of treating cancer.

SUMMARY OF THE INVENTION

The present invention relates generally to methods for the treatment of cancer. In particular, the invention relates to administration of glufosfamide alone or in combination with another anticancer agent for the treatment of cancer. Further, the present invention provides methods for the treatment of advanced and/or metastatic malignancies previously treated with chemotherapy.

In a first aspect, the present invention provides a method of treating cancer, which method comprises administering glufosfamide and gemcitabine in combination to a subject in need of such treatment. A variety of cancers can be treated by this method, for example pancreatic cancer, colorectal cancer, breast cancer, and the like.

In one embodiment, glufosfamide is administered for 1, 2, 3, 4, 5, 6, 7, 8, or more than 8 dosage cycles, each cycle comprises an infusion of glufosfamide in the range of:
a) about 1.5 to about 8.0 g/m$^2$; about 1.5 to about 6.0 g/m$^2$; about 1.5 to about 4.5 g/m$^2$; about 4.5 to about 8.0 g/m$^2$; about 4.5 to about 6.0 g/m$^2$; or about 4.5 to about 5.0 g/m$^2$ or over an infusion period of 1-6 hours once every three weeks;
b) about 1.5 to about 3.0 g/m$^2$ or about 1.5 to about 2.0 g/m$^2$ over an infusion period of 1-6 hours for three consecutive days (days 1, 2 and 3) every three weeks;
c) about 1.5 to about 2.0 g/m$^2$ over an infusion period of 1-6 hours once per week; or
d) about 1.5 to about 8.0 g/m$^2$; about 1.5 to about 6.0 g/m$^2$; or about 1.5 to about 4.5 g/m$^2$ over an infusion period of 1-6 hours once every four weeks.

In one embodiment, glufosfamide is administered for 1, 2, 3, 4 or more than 4 dosage cycles, wherein each cycle is a seven-week cycle. In one embodiment, glufosfamide is administered for 1, 2, 3, 4, 5, 6, or more than 6 dosage cycles, wherein each cycle is a three-week cycle. In one embodiment, glufosfamide is administered for 1, 2, 3, 4, 5, 6, or more than 6 dosage cycles, wherein each cycle is a four-week cycle.

In one embodiment, gemcitabine is administered for 1, 2, 3, 4, 5, 6, 7, 8 or more than 8 dosage cycles, and each cycle comprises an infusion of gemcitabine of:
a) about 1000 mg/m$^2$ over a period of about 30 min;
b) about 2200 mg/m$^2$ over a period of about 30 min; or
c) about 1500 mg/m$^2$ over a period of about 150 min.

In one embodiment, gemcitabine is administered on weeks 1, 2, 3, 5, 6 and 7 of a dosage cycle for 1, 2, 3, 4 or more than 4 dosage cycles, wherein each cycle is a seven-week cycle. In one embodiment, gemcitabine is administered on weeks 1, 2 and 3 of a dosage cycle for 1, 2, 3, 4, 5, 6, or more than 6 dosage cycles, wherein each cycle is a four-week cycle. Gemcitabine is administered one day before, one day after, or on the same day as, the administration of glufosfamide. In one embodiment, gemcitabine is administered on the same day as the administration of glufosfamide, about 30 minutes to about 4 hours after the administration of glufosfamide.

In a second aspect, the present invention provides a method of treatment comprising administering glufosfamide to a subject in need of treatment of advanced and/or metastatic malignancies previously treated with chemotherapy. In one aspect, the present invention provides methods for the treatment of a gemcitabine-refractory pancreatic cancer.

In another aspect, the invention provides a method for treating cancer, comprising administering an agent with antitumor activity, such as bevacizumab, irinotecan, exatecan, pemetrexed or cisplatin, in combination with glufosfamide or in combination with glufosfamide and gemcitabine.

DETAILED DESCRIPTION OF THE INVENTION

In an aspect of the invention, glufosfamide and gemcitabine are administered in combination to a subject in need of treatment for cancer. A variety of cancers can be treated by this method. An example of a cancer that can be treated by this method is pancreatic cancer. A third agent with antitumor activity, such as bevacizumab; topoisomerase I inhibitors e.g., irinotecan and exatecan; antifolates e.g., methotrexate, raltitrexed, lometrexol, and pemetrexed; or platinum based antineoplastic agent, e.g. carboplatin and cisplatin, can be administered in combination with glufosfamide and gemcitabine.

In an aspect of the invention, glufosfamide and bevacizumab are administered in combination to a subject in need of treatment for a cancer. A variety of cancers can be treated by this method. An example of a cancer that can be treated by this method is colorectal cancer.

In an aspect of the invention, glufosfamide and another anticancer agent selected from the group consisting of topoisomerase I inhibitors e.g., irinotecan and exatecan; antifolates e.g., methotrexate, raltitrexed, lometrexol, and pemetrexed; or platinum based antineoplastic agent e.g., carboplatin and cisplatin, are administered in combination to a subject in need of treatment for a cancer.

In an aspect of the invention, glufosfamide is administered to a subject in need of treatment for breast cancer. In another aspect of the invention, glufosfamide is administered to a subject in need of treatment for colorectal cancer. In another aspect of the invention, glufosfamide is administered to a subject in need of treatment for gemcitabine-refractory pancreatic cancer. For the aforementioned treatment of breast cancer, colorectal cancer, and gemcitabine-refractory pancreatic cancer glufosfamide is administered as a single agent (i.e., not in combination with another antineoplastic agent or another anticancer agent).

Glufosfamide, gemcitabine, bevacizumab, irinotecan, exatecan, pemetrexed, and cisplatin, as used in the present invention can be administered at any dose that is therapeutically effective, such as doses comparable to those routinely utilized clinically. Specific dose regimens for known and approved antineoplastic agents (e.g., the recommended effective dose) are known to physicians and are provided, for example, in the product descriptions found in the PHYSICIANS' DESK REFERENCE, 2003, 57th Ed., Medical Economics Company, Inc., Oradell, N.J.; Goodman & Gilman's THE PHARMACOLOGICAL BASIS OF THERAPEUTICS" 2001, $10^{th}$ Edition, McGraw-Hill, New York; and/or are available from the Federal Drug Administration and/or are discussed in the medical literature.

In an aspect, the invention provides a treatment method in which glufosamide, alone or in combination with another anticancer agent is administered according to a schedule or administration regimen discovered to be particularly effective for treatment.

Administration Regimens

It will be appreciated that chemotherapy for cancer sometimes involves multiple "rounds" or "dosage cycles" of administration of a drug, where each cycle comprises administration of the drug one or more times according to a specified schedule. A cycle is generally (but not necessarily) measured in weeks and can be, for example, 1, 2, 3, 4, 5, 6, 7, or 8 weeks in duration. In some embodiments, a cycle is longer than 8 weeks. For example, chemotherapeutic drugs can be administered for from 1 to 8 dosage cycles, or for a longer period. In some embodiments, the dosage cycle is a three-week cycle, a four-week cycle, or a seven-week cycle. In a dosage cycle, a drug is administered according to a specified schedule e.g., daily; once per week; multiple times a week either on consecutive days or non-consecutive days; once every cycle; multiple times every cycle such as every three weeks for three consecutive days; etc. When more than one drug (e.g., two drugs) is administered to a subject, each can be administered according to its own schedule as illustrated above (e.g., weekly; once every three weeks; etc.). It will be clear that administration of drugs, even those administered with different periodicity, can be coordinated so that both drugs are administered on the same day at least some of the time or, alternatively, so the drugs are administered on consecutive days at least some of the time.

In treatment regimens in which glufosfamide and gemcitabine (or another drug) are administered in combination, they can be administered in any order. In certain embodiments, glufosfamide is administered one day before, one day after, or on the same day as, administration of gemcitabine. In certain embodiments, gemcitabine is administered on the same day as glufosfamide; and administration of gemcitabine is commenced before, concurrent with, or after administration of glufosfamide. In certain embodiments, gemcitabine is administered (i.e. administration will begin) between about 30 minutes to about 4 hours after the administration of glufosfamide. It will be understood that other schedules can be used as determined by the physician.

In various embodiments, glufosfamide is administered to a patient in need of treatment for cancer for 1, 2, 3, 4, 5, 6, 7, 8, or more than 8 dosage cycles, each cycle comprising an infusion of glufosfamide in the range of:

a) about 1.5 to about 8.0 $g/m^2$; about 1.5 to about 6.0 $g/m^2$; about 1.5 to about 4.5 $g/m^2$; about 4.5 to about 8.0 $g/m^2$; about 4.5 to about 6.0 $g/m^2$; or about 4.5 to about 5.0 $g/m^2$ or over an infusion period of 1-6 hours once every three weeks;

b) about 1.5 to about 3.0 $g/m^2$ or about 1.5 to about 2.0 $g/m^2$ over an infusion period of 1-6 hours for three consecutive days (days 1, 2 and 3) every three weeks;

c) about 1.5 to about 2.0 $g/m^2$ over an infusion period of 1-6 hours once per week; or d) about 1.5 to about 8.0 $g/m^2$; about 1.5 to about 6.0 $g/m^2$; or about 1.5 to about 4.5 $g/m^2$ over an infusion period of 1-6 hours once every four weeks.

In one embodiment, glufosfamide is administered for 1, 2, 3, 4 or more than 4 dosage cycles, wherein each cycle is a seven-week cycle. In one embodiment, glufosfamide is administered for 1, 2, 3, 4, 5, 6, or more than 6 dosage cycles, wherein each cycle is a three-week cycle. In one embodiment, glufosfamide is administered for 1, 2, 3, 4, 5, 6, or more than 6 dosage cycles, wherein each cycle is a four-week cycle. As used in this context an "infusion period of 1-6 hours" includes an infusion period of about 1, about 2, about 3, about 4, about 5 and about 6 hours.

In various embodiments, gemcitabine is administered for 1, 2, 3, 4, 5, 6, 7, 8 or more than 8 dosage cycles, each cycle comprises an infusion of gemcitabine of:

a) about 1000 $mg/m^2$ over a period of about 30 min;

b) about 2200 $mg/m^2$ over a period of about 30 min; or c) about 1500 $mg/m^2$ over a period of about 150 min.

In one embodiment, gemcitabine is administered on weeks 1, 2, 3, 5, 6 and 7 of a dosage cycle for 1, 2, 3, 4 or more than 4 dosage cycles, wherein each cycle is a seven-week cycle. In one embodiment, gemcitabine is administered on weeks 1, 2 and 3 of a dosage cycle for 1, 2, 3, 4, 5, 6, or more than 6 dosage cycles, wherein each cycle is a four-week cycle. Gemcitabine is administered one day before, one day after, or on the same day as, the administration of glufosfamide. In one embodiment, gemcitabine is administered on the same day as the administration of glufosfamide, about 30 minutes to about 4 hours after the administration of glufosfamide.

As is understood in the art, treatment with cancer therapeutic drugs can be suspended temporarily if toxicity is observed, or for the convenience of the patient, without departing from the scope of the invention, and then resumed.

Administration in Combination

Two or three drugs are administered to a subject "in combination" when the drugs are administered as part of the same course of therapy. A course of therapy refers to administration of combinations of drugs believed by the medical professional to work together additively, complementarily, synergistically, or otherwise to produce a more favorable outcome than that anticipated for administration of a single drug. A course of therapy can be for one or a few days, but more often extends for several weeks.

Thus, an example of administration in combination is administration of glufosfamide once every three weeks for 1 to 8 three-week cycles beginning on day 1, and administration of gemcitabine once each week for weeks 1, 2, 3, 5, 6, and 7 of a seven-week cycle for one or more seven-week cycles. In an embodiment, administration of gemcitabine begins on day 1, day −1 (one day before day 1), or day 2 or another day, as administration of glufosfamide. Another example of administration in combination is administration of glufosfamide once every four weeks beginning on week 1 (on day 1) of a four-week cycle for 1 to 8 four-week cycles, and administration of gemcitabine on weeks 1, 2 and 3 (on days 1, 8 and 15) of a four-week cycle for 1 to 8 four-week cycles. In one embodiment, gemcitabine is administered on the same day as glufosfamide between about 30 minutes to about 4 hours after the administration of glufosfamide.

When two drugs are administered in combination, a variety of schedules can be used. In one case, for example and without limitation, Drug 1 is first administered prior to administration of Drug 2, and treatment with Drug 1 is continued throughout the course of administration of Drug 2; alternatively Drug 1 is administered after the initiation or completion of Drug 2 therapy; alternatively, Drug 1 is first administered contemporaneously with the initiation of the other cancer therapy. As used in this context, "contemporaneously" means the two drugs are administered the same day, or on consecutive days.

Although in principle certain drugs can be co-formulated, in general they are administered in separate compositions. Similarly, although certain drugs can be administered simultaneously, more often (especially for drugs administered by infusion) drugs are administered at different times on the same day, on consecutive days, or according to another schedule. For example, in one embodiment, glufosfamide is administered over a 4 hour infusion period once every four weeks beginning on day 1 of a four-week cycle and gemcitabine is administered over a 30 minute infusion period on days 1, 8 and 15 of a four-week cycle for 1 to 8 four-week cycles. On day 1, gemcitabine is administered 30 minutes after the administration of glufosfamide.

In some embodiments of the invention glufosfamide is administered as a "single agent," i.e., not administered "in combination" with another antitumor drug. For example, glufosfamide is administered to treat advanced and/or metastatic malignancies previously treated with chemotherapy. In one embodiment, the invention provides a method of administration of glufosfamide for treating locally advanced unresectable or metastatic pancreatic adenocarcinoma previously untreated with chemotherapy. In one embodiment, the invention provides a method of administration of glufosfamide for treating gemcitabine-refractory metastatic pancreatic adenocarcinoma.

Cancers

The methods of the present invention can be used for treatment of any cancer, including but not limited to breast cancer, pancreatic cancer, cancer of the colon and/or rectum, leukemia, skin cancer, bone cancer, prostate cancer, liver cancer, lung cancer, brain cancer, cancer of the larynx, gallbladder, parathyroid, thyroid, adrenal, neural tissue, head and neck, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, islet cell carcinoma, primary brain tumor, acute and chronic lymphocytic and granulocytic tumors, hairy-cell tumor, adenoma, hyperplasia, medullary carcinoma, pheochromocytoma, mucosal neuroma, intestinal ganglioneuroma, hyperplastic corneal nerve tumor, marfanoid habitus tumor, Wilm's tumor, seminoma, ovarian tumor, leiomyoma, cervical dysplasia and in situ carcinoma, neuroblastoma, retinoblastoma, soft tissue sarcoma, malignant carcinoid, topical skin lesion, mycosis fungoides, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, and epidermoid carcinomas.

Certain treatment regimens of the invention are particularly suited for treatment of pancreatic cancer, breast cancer, or colorectal cancer, as noted above. Thus, in certain embodiments of the invention the subject to whom treatment is administered has colorectal cancer or metastatic colorectal cancer. Colorectal cancer or metastatic colorectal cancer is currently treated by radiation therapy, surgery, and/or chemotherapy (e.g., administration of fluorouracil).

In certain embodiments of the invention, the subject to whom treatment is administered has breast cancer. Breast cancer is commonly treated by various combinations of surgery, radiation therapy, chemotherapy, and hormone therapy.

In certain embodiments of the invention, the subject to whom treatment is administered has pancreatic cancer. Among pancreatic cancers, chemotherapy-refractory pancreatic cancers, such as pancreatic cancers refractory to treatment with gemcitabine (see, e.g., Araneo et al., 2003, *Cancer Invest.* 21:489-96; Kozuch et al., 2001, *The Oncologist* 6:488-95; Noble and Goa, 1997, *Drugs* 54: 447-72N; Stephens et al., 1998, *Oncol. Nurs. Forum* 25:87-93; Burris and Storniolo, 1997, *Eur. J. Cancer* 33: Suppl 1:S18-22; Rothenberg et al., 1996, *Ann. Oncol.* 7:347-53) can be treated using the methods disclosed herein, e.g., by administration of glufosfamide. Serum carbohydrate 19-9 reportedly can be a useful marker for evaluating the response to gemcitabine therapy in pancreatic cancer (Ziske et al., 2003, *Br. J. Cancer* 89:1413-17). In one embodiment, response to glufosfamide therapy for cancer, wherein glufosfamide is administered as a single agent or in combination with another anticancer agent, is characterized by measuring the serum carbohydrate 19-9 levels of the subjects during treatment.

Subject

As used herein, "a subject" is a mammal in need of treatment for cancer. Generally, the subject is a human cancer patient. In some embodiments of the invention, the subject can be a non-human mammal such as a non-human primate, an animal used in a model system (e.g., animals such as mice and rats used in screening, characterization and evaluation of medicaments) and other mammals.

Treatment

As used herein, and as well-understood in the art, "treatment" is an approach for obtaining beneficial or desired medical results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment or if receiving a different treatment.

Chemotherapeutic Agents

The following section describes drugs used in various embodiments of the invention. As these drugs are well known, only brief discussions are provided. Publications cited in this section are intended to illustrate aspects of the drug for the benefit of the practitioner; however, citation to a particular publication in this section or elsewhere in this disclosure is not intended to limit the present invention in any respect, including as to doses, combinations, and indications.

Glufosfamide

The antitumor drug glufosfamide (β-D-glucosyl-ifosfamide mustard; glc-IPM) is an alkylating agent used for treatment of cancer (see U.S. Pat. No. 5,622,936 incorporated by reference herein and Niculescu-Duvaz, 2002, *Curr Opin Investig Drugs* 3:1527-32). The alkylating moiety (isophosphoramide mustard, IPM) is glycosidically linked to β-D-glucose, and cellular uptake of glufosfamide may be mediated by a sodium-dependent trans-membrane transporter protein of glucose (Briasoulis et al., 2000, *J Clin Oncol* 18:3535-44). In phase II clinical studies, glufosfamide has been administered to patients with pancreatic cancer receiving first line treatment and in patients with non-small cell lung cancer receiving second line chemotherapy, as well as glioblastoma, breast cancer and colon cancer patients (see Niculescu-Duvaz, 2002, supra). Glufosfamide is routinely administered intravenously; it is contemplated that in the practice of the present invention other administration routes also can be used, such as intrathecal administration, intratumoral injection, oral administration and others. Glufosfamide can be administered at doses comparable to those routinely utilized clinically (see Niculescu-Duvaz, 2002, supra). In preferred embodiments, glufosfamide is administered as described elsewhere herein.

Gemcitabine

Gemcitabine (2'-deoxy-2',2'-difluoro-cytidine, also known as 1-(4-amino-2-oxo-1H-pyrimidin-1-yl)-2-desoxy-2,2-difluororibose) is a nucleoside analogue that disrupts the process of cell replication. See U.S. Pat. Nos. 4,808,614 and 5,464,826, each of which is incorporated by reference herein. Gemcitabine HCl (Gemzar™; Lilly) has been used for treatment of patients with non-small cell lung cancer and pancreatic cancer. Gemcitabine HCl is routinely formulated as a sterile solution and is administered by intravenous infusion. Other salt forms, e.g., the monophosphate, sulfate, malonate, citrate, and succinate are readily prepared, and can be utilized if desired. It is contemplated that other administration routes can be used, including intratumor injection, intrathecal administration, and others. In preferred embodiments, gemcitabine is administered as described elsewhere herein.

Bevacizumab

Bevacizumab (Avastin™; Genentech) is an anti-vascular endothelial growth factor (VEGF) monoclonal antibody that has been developed as an anti-angiogenesis agent for treatment of cancers such as colorectal cancer, non-small-cell lung cancer, breast cancers, and other solid tumors. See Salgaller, 2003, *Curr Opin Mol Ther*, 5:657-67 and PCT applications WO 96/30046, and WO 98/45331. Bevacizumab as used in the present invention can be administered at doses comparable to those routinely utilized clinically (see, e.g., Yang, 2003, *N. Eng. J. Med.*, 349:419-21 and Cobleigh et al., 2003, *Semin Oncol.* 30 (5 Suppl 16):117-24.

Irinotecan

Irinotecan (CPT-11, Camptosar®; Pharmacia & Upjohn) is a semisynthetic derivative of the plant alkaloid camptothecin that inhibits topoisomerase I. It has been developed as an anti-cancer drug for the treatment of colorectal cancer. Irinotecan can be administered at doses comparable to those routinely utilized clinically. For example, and without limitation, patients can receive Camptosar® in a 90-minute infusion once every 3 weeks. The starting dose for most patients can be 350 mg/m$^2$, but the dose may decrease to 300 mg/m$^2$ for patients 70 years of age or older. Camptosar® can also be administered according to a weekly dosing schedule starting at 125 mg/m$^2$. The dose can be give for about 2 to 4 weeks, with course repeated every 7 weeks. See http://www.meds.com/colon/camptosar/treatment.html. Also see Rothenberg et al., 1996, *J Clin Oncol.* 14:1128-35.

Exatecan

Exatecan mesylate (DX-8951f; Daiichi Pharmaceutical Co.) is a water soluble analogue of the plant alkaloid camptothecin that inhibits topoisomerase I. Exatecan mesylate has been developed as a therapeutic agent for the treatment of non-small cell lung cancer, ovarian, tubal or peritoneal cancer, and breast cancer. Various dosages and administrations of exatecan mesylate for the treatment of cancers have been described. See, e.g., Verschraegen et al, 2004, *Cancer Chemother Pharmacol.* 53:1-7; Esteva et al., 2003, *Cancer* 98:900-7; Braybrooke et al., 2003, *Lung Cancer*, 41:215-9; Royce et al., 2004, *Invest New Drugs.* 22:53-61.

Pemetrexed

Pemetrexed (Alimta™), is an antifolate that inhibits thymidylate synthase, dibydrofolate reductase, glycinamide ribonucleotide formyltransferase, and aminoimidazole carboxamide ribonucleotide formyltransferase. Pemetrexed is active against pancreatic cancer cell lines in vitro and has shown activity in patients with advanced pancreatic cancer. See Kindler, 2002, *Semin Oncol.* 29:49-53 and Adjei, 2003, *Expert Rev Anticancer Ther.* 3:145-56.

Cisplatin

Cisplatin (cis-diaminedichloroplatinum (II)) is a divalent inorganic water soluble platinum containing complex with a broad activity as an antineoplastic agent (see Go and Adjei, 1999, *J Clin Oncol.* 17:409-22).

The present invention having been described in detail in the preceding sections, the following examples are provided to illustrate certain aspects of, but not to limit, the invention.

Example 1

Glufosfamide and Gemcitabine Combination Therapy

A combination of glufosfamide and gemcitabine was administered daily for 7 days to female NMRI nu/nu mice that were carrying tumors derived from HS766-T or As-PC-1 human pancreatic cancer cells. Mice were administered doses of vehicle control (0.9% sodium chloride solution, i.v.), gemcitabine (i.p.), glufosfamide (i.v.) or gemcitabine/glufosfamide combinations once daily for 7 consecutive days. A dose of 1.25 mg/kg was used as the standard dose for gemcitabine throughout the study.

In the HS766-T tumor model, administration of 10 mg/kg glufosfamide caused a dramatic delay in the onset of tumor growth compared with the gemcitabine alone or vehicle control groups. Gemcitabine treatment alone had only a marginal inhibitory effect on tumor progression. The combined administration of 10 mg/kg glufosfamide and 1.25 mg/kg gemcitabine resulted in a statistically significant (P=0.009) reduction of the test animals' tumor size at the end of the study period (Day 42) compared with treatment with glufosfamide alone. In the As-PC-1 tumor model, the dose regimens of glufosfamide and gemcitabine, either alone or in combination, had no apparent inhibitory effect on tumor growth. These results demonstrate that the HS766-T tumor model is sensitive to the combined administration of glufosfamide and gemcitabine.

Example 2

Glufosfamide and Gemcitabine Combination Therapy

A combination of glufosfamide and gemcitabine was administered to nude mice that were carrying tumors derived from type MiPaca2 human pancreatic cancer cells. Mice were administered doses of vehicle control, gemcitabine, glufosfamide, or gemcitabine/glufosfamide combinations as tabulated in Table 1 below (10 mice/group). Glufosfamide was administered i.v., daily for 14 days (Groups 1-4 and 7-12). Gemcitabine was administered at 300 mg/kg, i.p., once a week for three weeks (Groups 6 and 10-12). Gemcitabine was administered at 150 mg/kg, i.p., twice a week for three weeks (Groups 5 and 7-9).

TABLE 1

| Group | Glufosfamide (mg/kg) | Gemcitabine (mg/kg) |
|---|---|---|
| 1 * | 0 | 0 |
| 2 | 10 | 0 |
| 3 | 30 | 0 |
| 4 | 100 | 0 |
| 5 | 0 | 150 |
| 6 | 0 | 300 |
| 7 | 10 | 150 |
| 8 | 30 | 150 |
| 9 | 100 | 150 |
| 10 | 10 | 300 |
| 11 | 30 | 300 |
| 12 | 100 | 300 |

* = vehicle.

Groups 3 and 4 resulted in a modest reduction in tumor size. Approximately 50% reduction in tumor size was observed in Group 6. Group 10 was comparable to Group 6. Groups 11 and 12 demonstrated a greater reduction in tumor size compared to Group 6 (Group 12 appeared to be toxic). Gemcitabine at 150 mg/kg (Groups 5, 7-9 resulted in rapid deaths of the animals. These results demonstrate that administration of a combination of glufosfamide and gemcitabine resulted in tumor reduction in animals.

Example 3

Combination Therapy of Glufosfamide and Gemcitabine in Advanced Solid Tumors and Pancreatic Adenocarcinoma The following prophetic example is provided to illustrate treatment of cancer with glufosfamide and gemcitabine combination therapy. A clinical study is conducted to evaluate safety and demonstrate efficacy of glufosfamide in combination with gemcitabine. The pharmacokinetic parameters of glufosfamide (including isophosphoramide mustard, IPM) and gemcitabine (including dFdU) when administered in combination are also evaluated.

A multi-center study is conducted where subjects are divided into two groups: (i) subjects having locally advanced and/or metastatic solid tumors that have been previously treated or for whom there is no effective standard treatment available (Group I); and (ii) subjects having advanced/metastatic pancreatic adenocarcinoma previously untreated with chemotherapy (Group II). The subjects are assigned to cohorts.

The total duration of the study for each subject is up to 29 weeks, including up to 3 weeks prior to dosing (screening period). The treatment period is 8-weeks where glufosfamide is administered on day 1 of every 4-week cycle and gemcitabine is administered on days 1, 8 and 15 of each 4-week cycle. Glufosfamide (1500, 2500, 3500 and 4500 mg/m$^2$— one cohort at each dose level) is administered intravenously over 4 hours once every four weeks on day 1 of each cycle. One-quarter of the dose is administered over the first 30 minutes. The remaining three-quarters of the dose are administered over the following three and half hours. Gemcitabine (1000 mg/m$^2$) is administered weekly intravenously over 30 minutes on days 1, 8 and 15 of every 4-week cycle. On day 1 of each cycle, gemcitabine infusion begins 30 minutes after completion of the glufosfamide infusion. In subjects with stable disease or a complete or partial response after 2 cycles, the treatment is optionally extended for a period of up to 4 additional 4-week cycles. This dosing schedule is shown in Table 2 below:

TABLE 2

| Week (Day) | 1 (1) | 2 (8) | 3 (15) | 4 (28) |
|---|---|---|---|---|
| Glufosfamide | x | — | — | — |
| Gemcitabine | x | x | x | — |

Vital signs, electrocardiograms, clinical laboratory test results, and adverse events are used to assess safety. Tumor assessments, including computed tomography (CT) scans, are performed at baseline and every 8 weeks while subjects are on the study. Pharmacokinetic parameters are determined from plasma concentrations of glufosfamide and gemcitabine obtained at specific time intervals after dosing. Serial blood samples are collected from each subject for determination of plasma concentrations of glufosfamide/IPM (0.25, 0.5, 1, 1.5, 2, 3, 4, 4.25, 4.5, 5, 6, 8, 12, 16 and 24 hours after start of glufosfamide infusion on day 1 of cycles 1 and 2) and gemcitabine/dFdU (15, 30, 40, 50 minutes and 1, 1.5, 3.5, 7.5, 11.5 and 19.5 hours after start of gemcitabine infusion on days 1 and 8 of cycles 1 and 2). Blood samples are analyzed for glufosfamide and gemcitabine levels. All statistical tests used for the analysis of efficacy and safety data are two-sided and performed at 0.05 level of significance and the 90% confidence interval is computed.

The following pharmacokinetic parameters for glufosfamide/IPM and gemcitabine/dFdU are computed for each subject: time to maximum concentration ($T_{max}$); maximum peak observed concentration ($C_{max}$); the magnitude of the slope of the linear regression of the log concentration vs. time profile during the terminal phase ($K_{el}$); half-life, computed as 1 n (2)/$K_{el}$($T_{1/2}$); area under the concentration-time curve (AUC$_{last}$) from Hour 0 through the last quantifiable concentration time (LQCT), where LQCT is the time at which the last sample with a quantifiable concentration was drawn; Area under the concentration-time curve (AUC) from 0 to infinity, computed using the linear trapezoidal rule as AUC$_{last}$+$C_{LQCT}$/$K_{el}$; Clearance (Cl) computed as Dose divided by AUC (glufosamide and gemcitabine only); Apparent steady-state volume of distribution (Vss), computed as the Dose multiplied by AUMC/AUC$^2$, where AUMC is the area under the first moment of the plasma concentration time curve (glufosamide and gemcitabine only); Apparent volume of distribution in the post-distributive phase ($V_\beta$) computed as the ratio of Cl to the terminal elimination rate constant, $K_{el}$ (glufosamide and gemcitabine only). Dose-adjusted AUC and $C_{max}$ is calculated for each subject by dividing AUC and $C_{max}$ by dose. Efficacy outcomes are evaluated as determined by response rate, duration of response, progression-free survival, over all survival for pancreatic cancer subjects (6- and 12-month survival and change in serum carbohydrate 19-9). The combination therapy of glufosfamide with gemcitabine is improved over treatment with gemcitabine as a single agent.

Example 4

Glufosfamide Therapy for Gemcitabine-Refractory Metastatic Pancreatic Adenocarcinoma The following prophetic example is provided to illustrate treatment of gemcitabine-refractory metastatic pancreatic adenocarcinoma with glufosfamide therapy. A multi-center, randomized, open-label study is conducted to evaluate the safety and efficacy of glufosfamide in subjects with gemcitabine-refractory metastatic pancreatic adenocarcinoma as measured by overall survival compared with best supportive care.

Subjects are divided into two groups of 150 subjects per treatment group (i) glufosfamide treatment group (Group I) and (ii) best supportive care (BSC, Group II). Subjects in Group I are administered glufosfamide for duration of up to 51 weeks. Glufosfamide is administered intravenously over 6 hours once every 3 weeks at 4500 mg/m$^2$ for up to 17 doses. One-quarter of the dose is infused over 30 minutes and the remainder over the following five and half hours. Subjects may receive palliative radiotherapy but not within ±48 hours of a dose of glufosfamide. In order to assess the efficacy of glufosfamide treatment, subjects in Group II are not administered any medication that have antitumor effects e.g., chemotherapy or other systemic cytotoxic/cytostatic therapies. However, other appropriate supportive measures and concomitant medications that do not have antitumor effects, such as analgesics, antibiotics, transfusions, hematopoietic colony-stimulating factors (as therapy but not as prophylaxis), erythropoietin, megestrol acetate for appetite stimulation, are administered when appropriate. Subjects in Group I also receive best supportive care. This dosing schedule is shown in Table 3 below:

TABLE 3

| Week | 1 | 2 | 3 |
|---|---|---|---|
| Group I | x | — | — |
| Group II | — | — | — |

Tumor assessment is performed at baseline and every 6 weeks for the first 24 weeks and then every 9 weeks until disease progression are documented. Pharmacokinetic samples are collected from subjects in Group I during cycles 1 and 2. Blood samples for plasma concentrations of glufosfamide/IPM are collected at the following times on day 1 of cycles 1 and 2 from the subjects in Group I at the following time points: predose and immediately before completion of glufosfamide infusion. Additional pharmacokinetic parameters are measured for a subset of 24 subjects in Group I (AUC, $C_{max}$, and $T_{1/2}$ for glufosfamide/IPM). Blood samples are collected from this subset at the following times on day 1 of cycles 1 and 2: predose, 0.5 (immediately before changing the infusion rate), 1, 3, 6 (immediately before completion of glufosfamide infusion), 6.25, 6.5, 7, 8, 10, 16, 24 hours after the start of glufosfamide infusion.

The pharmacokinetic parameters (as described in Example 3 above) for glufosfamide/IPM (day 1 of cycles 1 and 2) are computed for each subject in the 24-subject subset. Efficacy outcomes are evaluated based on the response rate (complete response and partial response), duration of response, progression-free survival, 6- and 12-month survival, changes in VAS pain score and serum carbohydrate 19-9 response compared with best supportive care. Glufosfamide treated subjects with gemcitabine-refractory metastatic pancreatic adenocarcinoma have improved overall survival compared with best supportive care.

EQUIVALENTS AND INCORPORATION BY REFERENCE

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

The invention claimed is:

1. A method of treating pancreatic cancer comprising administering glufosfamide and gemcitabine in combination to a subject in need of such treatment.

2. The method of claim 1 wherein the cancer is a locally advanced and/or metastatic solid tumor.

3. The method of claim 1 wherein glufosfamide is administered for one or more dosage cycles, each cycle comprising an infusion of glufosfamide in the range of:

a) about 1.5 to about 8.0 g/m$^2$; about 1.5 to about 6.0 g/m$^2$; about 1.5 to about 4.5 g/m$^2$;

about 4.5 to about 8.0 g/m²; about 4.5 to about 6.0 g/m²; or about 4.5 to about 5.0 g/m² or over an infusion period of 1-6 hours once every three weeks;
b) about 1.5 to about 3.0 g/m² or about 1.5 to about 2.0 g/m² over an infusion period of 1-6 hours for three consecutive days (days 1, 2 and 3) every three weeks;
c) about 1.5 to about 2.0 g/m² over an infusion period of 1-6 hours once per week; or
d) about 1.5 to about 8.0 g/m²; about 1.5 to about 6.0 g/m²; or about 1.5 to about 4.5 g/m² over an infusion period of 1-6 hours once every four weeks.

4. The method of claim 1 wherein gemcitabine is administered once each week of a seven-week dosage cycle, wherein said administration is for one or more seven-week cycles, and wherein each cycle comprises an infusion of gemcitabine of:
   a) about 1000 mg/m² over a period of about 30 min;
   b) about 2200 mg/m² over a period of about 30 min; or
   c) about 1500 mg/m² over a period of about 150 min.

5. The method of claim 1 wherein gemcitabine is administered weeks 1, 2 and 3 of a four-week cycle for one more four-week cycles, and wherein each cycle comprises an infusion of gemcitabine of:
   a) about 1000 mg/m² over a period of about 30 min;
   b) about 2200 mg/m² over a period of about 30 min; or
   c) about 1500 mg/m² over a period of about 150 min.

6. The method of claim 5 wherein each cycle comprises an infusion of glufosfamide in the range of about 1.5 to about 4.5 g/m² over an infusion period of 1-6 hours once every four weeks.

7. The method of claim 6 wherein gemcitabine is administered on the same day as the administration of glufosfamide.

8. The method of claim 7 wherein gemcitabine is administered between about 30 minutes to about 4 hours after the administration of glufosfamide.

9. A method of treating pancreatic cancer comprising administering glufosfamide and gemcitabine in combination to a subject in need of such treatment wherein glufosfamide is administered for one or more dosage cycles, each cycle comprising:
   a) an infusion of glufosfamide in the range of about 1.5 to about 8.0 g/m²; about 1.5 to about 6.0 g/m²; or about 1.5 to about 4.5 g/m² over an infusion period of 1-6 hours once every four weeks; and
   b) an infusion of gemcitabine of about 1000 mg/m² over a period of about 30 min.

10. The method of claim 9 wherein each cycle comprises an infusion of glufosfamide in the range of about 1.5 to about 4.5 g/m² over an infusion period of 1-6 hours once every four weeks.

11. The method of claim 9 wherein gemcitabine is administered on the same day as the administration of glufosfamide.

12. The method of claim 11 wherein gemcitabine is administered between about 30 minutes to about 4 hours after the administration of glufosfamide.

13. The method of claim 12 wherein glufosfamide is administered once every four weeks as an infusion in the range of about 1.5 to about 4.5 g/m² over an infusion period of 4 hours and gemcitabine is administered 30 minutes after the administration of glufosfamide.

14. A method of treating gemcitabine-refractory pancreatic cancer, comprising administering to a human subject in need thereof an effective amount of glufosfamide.

15. The method of claim 14 wherein glufosfamide is administered for one or more dosage cycles, each cycle comprising an infusion of glufosfamide in the range of:
   a) about 1.5 to about 8.0 g/m²; about 1.5 to about 6.0 g/m²; about 1.5 to about 4.5 g/m²; about 4.5 to about 8.0 g/m²; about 4.5 to about 6.0 g/m²; or about 4.5 to about 5.0 g/m² or over an infusion period of 1-6 hours once every three weeks;
   b) about 1.5 to about 3.0 g/m² or about 1.5 to about 2.0 g/m² over an infusion period of 1-6 hours for three consecutive days (days 1, 2 and 3) every three weeks;
   c) about 1.5 to about 2.0 g/m² over an infusion period of 1-6 hours once per week; or
   d) about 1.5 to about 8.0 g/m²; about 1.5 to about 6.0 g/m²; or about 1.5 to about 4.5 g/m² over an infusion period of 1-6 hours once every four weeks.

16. The method of claim 14, wherein glufosfamide is administered for one or more dosage cycles, each cycle comprising an infusion of glufosfamide in the range of about 1.5 to about 6.0 g/m² over an infusion period of 1-6 hours once every three weeks.

17. The method of claim 16 wherein each cycle comprises an infusion of about 4.5 g/m² glufosfamide over an infusion period of 1-6 hours once every three weeks.

* * * * *